(12) United States Patent
Hu et al.

(10) Patent No.: US 9,066,870 B2
(45) Date of Patent: Jun. 30, 2015

(54) METHODS FOR DRUG DELIVERY COMPRISING UNFOLDING AND FOLDING PROTEINS AND PEPTIDE NANOPARTICLES

(75) Inventors: Yiqiao Hu, Jiangsu (CN); Jinhui Wu, Jiangsu (CN); Dawei Ding, Jiangsu (CN); Guangming Gong, Jiangsu (CN); Xiaolei Tang, Jiangsu (CN); Chunhui Tong, Jiangsu (CN); Yan Zhu, Jiangsu (CN); Shaoling Li, Sunnyvale, CA (US)

(73) Assignees: Nanjing University, Nanjing (CN); Nanjing Effect Pharm Drug Development Corporation, Nanjing (CN)

( * ) Notice: Subject to any disclaimer, the term of this patent is extended or adjusted under 35 U.S.C. 154(b) by 378 days.

(21) Appl. No.: 12/851,600

(22) Filed: Aug. 6, 2010

(65) Prior Publication Data
US 2011/0059181 A1    Mar. 10, 2011

Related U.S. Application Data

(63) Continuation-in-part of application No. PCT/CN2009/073180, filed on Aug. 10, 2009.

(51) Int. Cl.
| | |
|---|---|
| A61K 9/16 | (2006.01) |
| A61K 9/28 | (2006.01) |
| B01J 13/00 | (2006.01) |
| B05D 3/00 | (2006.01) |
| A61K 9/19 | (2006.01) |
| A61K 9/51 | (2006.01) |

(52) U.S. Cl.
CPC ............. *A61K 9/19* (2013.01); *A61K 9/5138* (2013.01); *A61K 9/5192* (2013.01)

(58) Field of Classification Search
CPC ...... A61K 9/19; A61K 9/5192; A61K 9/5138
See application file for complete search history.

(56) References Cited

U.S. PATENT DOCUMENTS

| | | | |
|---|---|---|---|
| 4,582,719 A * | 4/1986 | Kaetsu et al. | 514/773 |
| 4,671,954 A | 6/1987 | Goldberg et al. | |
| 4,996,988 A * | 3/1991 | Ohhara et al. | 600/300 |
| 5,560,933 A | 10/1996 | Soon-Shiong et al. | |
| 6,749,868 B1 * | 6/2004 | Desai et al. | 424/491 |
| 2002/0103517 A1 | 8/2002 | West et al. | |
| 2002/0192280 A1 * | 12/2002 | Hunter et al. | 424/465 |
| 2003/0187062 A1 * | 10/2003 | Zenoni et al. | 514/449 |
| 2006/0121119 A1 * | 6/2006 | Zenoni et al. | 424/489 |
| 2007/0087022 A1 | 4/2007 | Desai et al. | |
| 2007/0122799 A1 | 5/2007 | Vodyanoy et al. | |
| 2007/0134332 A1 | 6/2007 | Turnell et al. | |
| 2008/0317670 A1 | 12/2008 | Miao et al. | |
| 2009/0324671 A1 | 12/2009 | Ngo et al. | |
| 2010/0112072 A1 | 5/2010 | Wang et al. | |

FOREIGN PATENT DOCUMENTS

| | | | |
|---|---|---|---|
| EP | 1683517 A1 | 7/2006 | |
| JP | S56-115713 | 9/1981 | |
| WO | WO 98/14174 * | 4/1998 | ............... A61K 9/14 |
| WO | 2006/033679 A2 | 3/2006 | |
| WO | 2007027941 | 3/2007 | |
| WO | 2007069272 | 6/2007 | |
| WO | 2008/013785 A2 | 1/2008 | |
| WO | 2008/124465 A2 | 10/2008 | |

OTHER PUBLICATIONS

Matsuura et al. Artificial Peptide-Nanospheres Self-Assemebled from Three-Way Junctions of beta-Sheet-Forming Peptides. JACS Communications, Published on the Web Jun. 30, 2005, vol. 127, pp. 10148-10149.*
Fuchs et al. Paclitaxel: An Effective Antineoplastic Agent in the Treatment of Xenotransplanted Hepatoblastoma. Medical and Pediatric Oncology, vol. 32, pp. 209-215.*
Neurath et al. The Chemistry of Protein Denaturation. Chemical Reviews, 1944, vol. 34, No. 2, pp. 157-265.*
Timasheff. The Control of Protein Stability and Association by Weak Interactions with Water: How Do Solvents Affect These Processes? Annu. Rev. Biophys. Biomol. Struct. 1993, vol. 22, pp. 67-97.*
Fuchs et al. Paclitaxel: An Effective Antineoplastic Agent in the Treatment of Xenotransplanted Hepatoblastoma. Medical and Pediatric Oncology. vol. 32, 1999, pp. 209-215.*
Yu, et al., "Spray freezing into liquid nitrogen for highly stable protein nano structured microparticles," European Journal of Pharmaceutics and Biopharmaceutics [online], Jul. 2, 2004, [retrieved on Sep. 29, 2010], vol. 58, Iss. 3, pp. 529-537, Retrieved from the Internet: <URL: http://www.sciencedirect.com/science/journal/09396411>, entire document.
Yeo, et al., "Microencapsulation Methods for Delivery of Protein Drugs," Biotechnology and Bioprocess Engineering [online], Aug. 1, 2001, [Retrieved on Sep. 29, 2010], vol. 6, Issue 4, pp. 213-230, Retrieved from the Internet: <URL: http://www.bbe.or.kr/home/journal/>, entire document.
International Search Report for International Patent Application No. WO2011/019585, dated Sep. 27, 2010.
Written Opinion for International Patent Application No. WO2011/019585, dated Sep. 27, 2010.
Aubin-Tam, et al. "Structure and function of nano particle protein conjugates," Biomedical Materials [online], Aug. 8, 2008, [retrieved on Sep. 29, 2010], vol. 3, No. 3, pp. 1-17, Retrieved from the Internet: <URL: http://iopscience.iop.org/1748-605X/>, entire document.

* cited by examiner

*Primary Examiner* — Marcela M Cordero Garcia
(74) *Attorney, Agent, or Firm* — Lisa V. Mueller; Michael Best & Friedrich LLP (57) ABSTRACT

The present invention provides preparation methods of protein nanoparticles for in vivo delivery of pharmacologically active agents, wherein said methods are to encase pharmaceutically active agents into proteins or peptides to form nanoparticles by unfolding the protein, and subsequently refolding or assembling the protein to produce a pharmacologically active agent encased within a protein nanoparticle.

25 Claims, 6 Drawing Sheets

Fig. 1

EFFECTS OF VARIOUS pH VALUES ON THE PARTICLE SIZES OF THE PACLITAXEL-ALBUMIN NANOPARTICLES (15% LOADING PROTEIN)

Fig. 2

PARTICLE SIZE DISTRIBUTION OF THE
PACLITASXEL-ALBUMIN NANOPARTICLES

Fig. 3
TEM PICTURE OF THE PACLITAXEL-ALBUMIN NANOPARTICLES
PREPARED ACCORDING TO THE METHODS OF CURRENT
INVENTIONS (DRUG LOADING: 10:59&)

Fig. 4

HIGH RESOLUTION TEM IMAGES (a) PACLITAXEL-ALBUMIN NANOPARTICLES;
(b) TEM IMAGE OF BLANK ALBUMIN NANOPARTICLES;
(c) TEM IMAGE OF FREE PACLITAXEL;
(d) TEM IMAGE OF PACLITAXEL-ALBUMIN NANOPARTICLES

Fig. 5

X-RAY POWDER DIFFRACTION PATTERNS
(a) PACLITAXEL;
(b) ALBUMIN NANOPARTICLES;
(c) PACLITAXEL-ALBUMIN NANOPARTICLES (DRUG LOADING = 12.9%);
(d) ALBUMIN AND PACLITAXEL (12.9%)]

Fig. 6

PRACLITAXEL-ALBUMIN NANOPARTICLES AND ABRAZANE® SOLUTIONS (a) 2mg/ml PACLITAXEL-ALBUMIN;
(b) 2mg/ml ABRAZANE®;
(c) 20mg/ml PACLITAXEL-ALBUMIN;
(d) 20mg/ml ABRAZANE®;
(e) 50mg/ml PACLITAXEL-ALBUMIN;
(f) 50mg/ml ABRAZANE®

US 9,066,870 B2

METHODS FOR DRUG DELIVERY COMPRISING UNFOLDING AND FOLDING PROTEINS AND PEPTIDE NANOPARTICLES

CROSS-REFERENCE TO RELATED APPLICATIONS

This is a continuation-in-part of International Patent Application No. PCT/CN2009/073180, filed on Aug. 11, 2009, the contents of which are hereby incorporated by reference.

FIELD OF THE INVENTION

The present invention relates to in vivo delivery of pharmacologically active agents and clinical use thereof. Specifically, the invention provides methods for encasing pharmaceutically active agents into proteins or peptides to form nanoparticles by unfolding the protein, and subsequently refolding or assembling the protein to create a nanoparticle. Produced particles comprise about 1 to about 40% by weight of pharmacologically active agents and have the diameter in the range of about 5 to about 500 nm or more.

BACKGROUND OF THE INVENTION

Intravenous administration of pharmacologically active agents offers rapid and direct equilibration with the blood stream which carries the medication to the rest of the body. To decrease the side effects of the intravenous administrated agents, encapsulation of agents to micro- or nano-particles is a useful method. In one aspect, intravenous injection of the therapeutic particles would allow gradual release of the drugs inside the intravascular compartment. In another aspect, drugs in the therapeutic particles would be target delivered when the therapeutic particles are made from target materials.

Some methods of preparing protein particles, such as those used by Abraxane® (U.S. Pat. No. 6,749,868, U.S. Pat. No. 5,560,933), homogenized a mixture of protein solution and organic solvent to form an emulsion, and then subjected the emulsion to a high pressure homogenizer. Under the high pressure, albumin will form a shell around the paclitaxel particle center. Besides the complexity of these methods, high pressure and relatively high temperature are required for obtaining nanoparticles and removing organic solvent. Use of organic solvents is undesirable due to its toxicity and the need to control residual. In addition, drug loading capabilities are limited likely due to the limitation of relying on physical forces to open disulfide bridges. Meanwhile, due to the high pressure and shearing force during the preparation, proteins or peptides may denature permanently, and therefore may lose their bioactivity.

Protein particles have been reported in the literatures as carriers of pharmacologically or diagnostic agents. Microspheres of albumin have been prepared by either heat crosslinking or chemical crosslinking. For instance, the literature has disclosed the use of albumin as a drug carrier for taxanes, including paclitaxel and doxorubicin derivatives. [See Journal of Controlled Release 132 (2008) 171-183; Advanced Drug Delivery Reviews 60 (2008) 876-885]. Further, additional references have disclosed the use of protein cages for drug delivery [Small 5 (2009) 1706-1721]. However, the drug delivery systems cited in the literature are limited by their drug loading capacity as well as limitations as to the therapeutic agents that may be incorporated into the drug delivery systems.

Heat crosslinked microspheres are produced from an emulsified mixture (e.g., albumin, the agent to be incorporated, and suitable oil) at temperatures between 100° C. and 150° C. The microspheres are then washed with a suitable solvent and stored. Leucuta et al. [International Journal of Pharmaceutics Vol. 41:213-217 (1988)] describe the method of preparation of heat crosslinked microspheres.

The procedure for preparing crosslinked microspheres, as described in the literature [Science Vol. 213:233-235 (1981)] and U.S. Pat. No. 4,671,954, uses glutaraldehyde to crosslink the protein chemically, followed by washing and storage.

The reported methods for preparation of protein nanoparticles provide difficulty in encapsulating water-insoluble agents. This limitation is caused by the method itself that relies on crosslinking of proteins in the aqueous phase of an emulsion. Any aqueous-soluble agent dissolved in the protein-containing aqueous phase may be entrapped within crosslinked protein matrix, but a poorly water-soluble or oil-soluble agent cannot be incorporated into a protein matrix formed by these techniques. Furthermore, the protein used for encapsulation is often already denatured and their bioactivity is easily lost during the preparation.

BRIEF DESCRIPTION OF THE INVENTION

The present invention provides, in one embodiment, a method for the preparation of nanoparticles encasing a pharmacologically active agent within a protein for in vivo delivery, wherein said method comprises the following steps: (a) preparing or obtaining a protein solution comprising a protein in combination with a first solvent; and (b) contacting said pharmacologically active agent with said protein solution of step (a) in the presence of a solution suitable for unfolding the protein, thereby causing unfolding of said protein, and subsequent refolding or assembling of said protein to encase said pharmacologically active agent within said protein. The nanoparticles generally have an average diameter ranging from about 5 nm to about 2000 nm, preferably from about 25 nm to about 500 nm, and even more preferably from about 50 nm to about 300 nm. The nanoparticles produced by the method of the current embodiment may generally include from about 1% to about 40% of pharmacologically active agent by total weight of the nanoparticle.

Additionally, the pharmacologically active agent is generally a hydrophobic agent, such as paclitaxel, docetaxel, irinotecan, fluorouracil, carmustine, doxorubicin, phenesterine, piposulfan, tamoxifen, lomustine, gambogic acid, oridonin, podophyllotoxin, atorvastatin, simvastatin, fenofibrate, nifedipine, ibuprofen, indomethacin, piroxicam, glyburide, diazepam, risperidone, ziprasidone, tacrolimus, rapamycin, indinavir, ritonavir, telaprevir, lopinavir, and combinations thereof. In a preferred embodiment, the hydrophobic pharmacologically active agent may include paclitaxel and docetaxel. The active agent may also comprise a hydrophilic compound. Examples of hydrophilic compounds within the scope of the current invention include, but are not limited to, cyclophosphamide, bleomycin, daunorubicin, epirubicin, methotrexate, fluorouracil and its analogues, platinum and analogues, vinblastine and analogues, homoharringtonine and its derivatives, actinomycin-D, mitomycin-c, and etoposide. Further, the method of the current embodiment generally incorporates proteins comprising albumin, transferrin, insulin, endostatin, hemoglobin, myoglobin, lysozyme, immunoglobulins, α-2-macroglobulin, fibronectin, lamin, collagen, gelatin, artificial peptides and proteins, and combinations thereof. In a preferred embodiment of the current invention, the protein may include albumin, transferrin, insulin, endostatin, and hemoglobin. The method of the current embodiment also may incorporate a first solvent used in step (a) including water, saline, sugar, lyophilization protectants, and protein stabilizers. In preferred embodiments, the first solvent may include water phosphate, acetate, glycine, tris(hydroxymethyl)aminomethane, aqueous solutions containing hydrogen peroxide, aqueous solutions comprising glutathione, sodium chloride solutions, glucose solutions, mycose, mannitol, sucrose, acetyltryptophan, sodium caprylate and combinations thereof. Step (a) of the method of the current embodiment may be performed at a temperature generally ranging from about −20° C. to about 100° C., preferably from about 50° C. to about 85° C., and more preferably from about 55° C. to about 75° C. Furthermore, step (a) of the method of the current embodiment may be conducted at pH levels of about 3 to about 9, about 5 to about 8.5, and about 6 to about 8.

In addition, the unfolding solution of step (b) generally comprises water, strong acids, strong bases, inorganic salts, organic solvents, denaturants, and surfactants. In preferred embodiments, the unfolding solution may include methanol, ethanol, propanol, isopropanol, formaldehyde, chloroform, acetone, hydrogen sulfide, 2-mercaptoethanol, dithiothreitol, guanidine, urea, perchlorate, tri-n-butylphosphine, captopril, performic acid, penicillamine, glutathione, methimazole, acetylcysteine, 3,3",3"-phosphinidynettripropionic acid, and combinations thereof. The unfolding process of step (b) may also incorporate external stress capable of aiding in the unfolding of the protein. The external stress may include temperature changes, pressure changes, mechanical forces, radiation, and combinations thereof. Specifically, applying pressure to the reaction in the range of about 100 to about 100,000 pounds per square inch (psi) may aid in the unfolding of the protein. In another embodiment, applying pressure to the reaction in the range of about 2000 to about 60,000 pounds per square inch (psi) may aid in the unfolding of the protein.

Moreover, the method of the current embodiment may also include a dialysis or filtration step (c) to remove impurities and create a more concentrated solution of nanoparticles. The method of the current embodiment may further include a step whereby the concentrated solution of nanoparticles of step (c) is subjected to a dehydration process to obtain dried nanoparticles, by means such as lyophilization, spray drying or vacuum dehydration. The dried nanoparticles may be incorporated into a pharmaceutical dosage form.

In another embodiment, the present invention includes a method for the preparation of nanoparticles encasing a hydrophobic pharmacologically active agent within a protein for in vivo delivery, wherein said method comprises the following steps: (a) preparing or obtaining a protein solution at a temperature ranging from about −20° C. to about 100° C., and a pH ranging from about 3 to about 9; and (b) contacting said hydrophobic pharmacologically active agent with said solution of step (a) in the presence of a solution suitable for unfolding, thereby causing unfolding of said protein, and subsequent refolding or assembling of said protein to encase said pharmacologically active agent within said protein. The nanoparticles have a diameter ranging from about 5 nm to about 500 nm and said nanoparticles comprise about 1% to about 40% of pharmacologically active agent by total weight of the nanoparticle. The hydrophobic pharmacologically active agent may include, but is not limited to paclitaxel, docetaxel, irinotecan, carmustine, doxorubicin, phenesterine, piposulfan, tamoxifen, lomustine, gambogic acid, oridonin, podophyllotoxin, atorvastatin, simvastatin, fenofibrate, nifedipine, ibuprofen, indomethacin, piroxicam, glyburide, diazepam, risperidone, ziprasidone, tacrolimus, rapamycin, indinavir, ritonavir, telaprevir, lopinavir, and combinations thereof. The protein of the method of the current embodiment may include, but is not limited to albumin, transferrin, insulin, endostatin, hemoglobin, myoglobin, lysozyme, immunoglobulins, α-2-macroglobulin, fibronectin, lamin, collagen, gelatin, artificial peptides and proteins, and combinations thereof. The method of this embodiment includes a first solvent comprising water, saline, phosphate, acetate, glycine, tris(hydroxymethyl)aminomethane, aqueous solutions containing hydrogen peroxide, aqueous solutions comprising glutathione, sodium chloride solutions, glucose solutions, mycose, mannitol, sucrose, acetyltryptophan, sodium caprylate and combinations thereof. Further, the unfolding solution of the method of this embodiment comprises methanol, ethanol, propanol, isopropanol, formaldehyde, chloroform, acetone, hydrogen sulfide, 2-mercaptoethanol, dithiothreitol, guanidine, urea, perchlorate, tri-n-butylphosphine, captopril, performic acid, penicillamine, glutathione, methimazole, acetylcysteine, 3,3",3"-phosphinidynettripropionic acid, and combinations thereof.

In a further embodiment, the present invention comprises a method for the preparation of nanoparticles encasing paclitaxel within a protein for in vivo delivery, wherein said method comprises the following steps: (a) preparing or obtaining a protein solution comprising a protein in combination with a first solvent at a temperature ranging from about 55° C. to about 75° C., and a pH ranging from about 6 to about 8; (b) contacting said paclitaxel with said protein solution of step (a) in the presence of an unfolding solution, thereby causing unfolding of said protein, and subsequent refolding or assembling of said protein to encase said paclitaxel within said protein; (c) optionally dialyzing or filtering said nanoparticles to remove excess chemicals to obtain a more concentrated solution; and (d) subjecting said concentrated solution of nanoparticles of step (c) to a dehydration process to produce preserved nanoparticles capable of incorporation into a pharmaceutical dosage form; wherein the nanoparticles have an average diameter ranging from about 50 nm to about 300 nm and the nanoparticles comprise about 1% to about 40% of pharmacologically active agent by total weight of the nanoparticle. In this embodiment, the unfolding solution is selected from the group consisting of ethanol, acetone, hydrogen sulfide, 2-mercaptoethanol, urea, and combinations thereof. Further, the protein incorporated into the method of this embodiment is selected from the group consisting of albumin, transferrin, insulin, endostatin, and hemoglobin.

In yet another embodiment, the present invention comprises a method for the preparation of nanoparticles encasing docetaxel within a protein for in vivo delivery, wherein said method comprises the following steps: (a) preparing or obtaining a protein solution comprising a protein in combination with a first solvent at a temperature ranging from about 55° C. to about 75° C., and a pH ranging from about 6 to about 8; (b) contacting said docetaxel with said protein solution of step (a) in the presence of an unfolding solution, thereby causing unfolding of said protein, and subsequent refolding or assembling of said protein to encase said docetaxel within said protein; (c) optionally dialyzing or filtering said nanoparticles to remove excess chemicals to obtain a more concentrated solution; and (d) subjecting the concentrated solution of nanoparticles of step (c) to a dehydration process to produce preserved nanoparticles capable of incorporation into a pharmaceutical dosage form; wherein the nanoparticles have an average diameter ranging from about 50 nm to about 300 nm and the nanoparticles comprise about 1% to about 40% of pharmacologically active agent by total weight of the nanoparticle. In this embodiment, the unfolding solution is selected from the group consisting of ethanol, acetone, hydrogen sulfide, 2-mercaptoethanol, urea, and combinations thereof. Further, the protein incorporated into the method of this embodiment is selected from the group consisting of albumin, transferrin, insulin, endostatin, and hemoglobin.

In a further embodiment, the current invention includes a method of treating cancer comprising the steps of: (a) producing a nanoparticle according to the processes described herein; and (b) administering the nanoparticle to a patient in need thereof.

In another embodiment, the current invention includes a nanoparticle comprising a pharmacologically active agent encased within a protein, wherein said nanoparticle is suitable for in vivo delivery, and wherein said nanoparticle is produced according to the following steps: (a) preparing or obtaining a protein solution comprising said protein in a first solvent at a temperature ranging from about −20° C. to about 100° C., and a pH ranging from about 3 to about 9; and (b) contacting said hydrophobic pharmacologically active agent with said solution of step (a) in the presence of an unfolding solution, thereby causing unfolding of said protein, and subsequent refolding or assembling of said protein to encase said pharmacologically active agent within said protein.

In an additional embodiment, the current invention includes a nanoparticle comprising paclitaxel encased within a protein, wherein said nanoparticle is suitable for in vivo delivery, and wherein said nanoparticle is produced according to the following steps: (a) dissolving said protein in a first solvent at a temperature ranging from about 55° C. to about 75° C., and a pH ranging from about 6 to about 8; (b) contacting said paclitaxel with said protein solution of step (a) in the presence of an unfolding solution, thereby causing unfolding of said protein, and subsequent refolding or assembling of said protein to encase said paclitaxel within said protein; (c) optionally dialyzing or filtering said nanoparticles to remove excess chemicals to obtain a more concentrated solution; and (d) subjecting the concentrated solution of nanoparticles of step (c) to a dehydration process to produce preserved nanoparticles capable of incorporation into a pharmaceutical dosage form.

In still another embodiment, the current invention includes a nanoparticle comprising docetaxel encased within a protein, wherein said nanoparticle is suitable for in vivo delivery, and wherein said nanoparticle is produced according to the following steps: (a) preparing or obtaining a protein solution comprising said protein in a first solvent at a temperature ranging from about 55° C. to about 75° C., and a pH ranging from about 6 to about 8; (b) contacting said docetaxel with said protein solution of step (a) in the presence of an unfolding solution, thereby causing unfolding of said protein, and subsequent refolding or assembling of said protein to encase said docetaxel within said protein; (c) optionally dialyzing or filtering said nanoparticles to remove excess chemicals to obtain a more concentrated solution; and (d) subjecting the concentrated solution of nanoparticles of step (c) to a dehydration process to produce preserved nanoparticles capable of incorporation into a pharmaceutical dosage form.

DETAILED DESCRIPTION OF THE INVENTION

In this invention, there are provided preparation methods for nanoparticles encasing a pharmacologically active agent within a protein for in vivo delivery, wherein the method comprises the following steps: (a) preparing or obtaining a protein solution comprising a combination of; and (b) contacting the pharmacologically active agent with the solution of step (a) in the presence of an unfolding solution, thereby causing unfolding of said protein, and subsequent refolding or assembling of said protein to encase the pharmacologically active agent within the protein. In accordance with the present invention, it has been discovered that when proteins or peptides are unfolded by external stress or compounds and then refolded or reassembled, pharmacologically active agents can be encased into proteins or peptides to form nanoparticles with the diameter in the range of about 5 nm to about 2000 nm. The loading of pharmacologically active agents is about 1% to about 40% (w/w).

The current invention represents an improvement over the prior art in several aspects. First, nanoparticles formed by the methods of the current invention may be able to bind up to 90% of the added pharmacologically active agent, an amount that exceeds prior art methods and creates a more efficient process and cost-effective method. Additionally, the current invention allows for a drug loading capacity of up to about 40%, such that about 40% of the weight of the nanoparticle may comprise the pharmacologically active agent. Due to the higher drug loading capacity, the skilled artisan will be able to achieve smaller drug volumes for administration to the patient, shorter administration times, and thus better patient compliance. The higher drug loading capacity decreases the amount of protein used to deliver the pharmacologically active agent, which also improves the cost-efficiency of the product. Further, prior art drug delivery systems with smaller drug loading capacities were not capable of adequately delivering pharmacologically active agents requiring high doses, due to the large volume of delivery particles that would be required to deliver an effective dose. However, with the high drug loading capacity of the nanoparticles created by the process of the current invention, this limitation is decreased significantly.

Another benefit of the current invention is that it can selectively deliver pharmacologically active agents for clinical use. Particles prepared from the methods described herein allow some targeting to certain organs and body systems. For instance, when the protein carrier is albumin, targeting to the liver, lungs, spleen or lymphatic circulation is feasible by varying the size of particles. When the protein carriers are transferrin or insulin, whose receptors are highly expressed on the tumor cells surface, pharmacologically active agents can be selectively delivered to tumor tissue because of the affinity between ligands and receptors expressed on the surface of tumor cells. When the protein carrier is endostatin, whose receptor is mainly located on the new blood vessel, the nanoparticle will accumulate in the tumor tissue because there are a huge amount of new blood vessels in tumor tissue.

In some way, targeting to different tissues would be allowed by varying different protein carriers. Accordingly, the current invention provides a more efficient, cost effective method for delivering pharmacologically active agents to targeted areas of the body.

As used herein, the term "in vivo delivery" refers to delivery of a pharmacologically active agent by such routes of administration as oral, intravenous, subcutaneous, intraperitoneal, intrathecal, intranasal, intramuscular, inhalational, topical, transdermal, rectal (suppositories), vaginal, and the like.

As used herein, the term "nanoparticle" refers to a small unit that behaves as a whole unit in terms of its transport and properties. The nanoparticles of the current invention generally have an average particle diameter ranging from about 5 nanometers (nm) to about 2000 nm. In a preferred embodiment, the average particle diameter of the nanoparticle ranges from about 25 nm to about 500 nm. In an even more preferred embodiment of the current invention, the average nanoparticle diameter ranges from about 50 nm to about 300 nm. Further, the nanoparticles of the current invention are capable of binding a pharmacologically active agent (active agent), such that up to about 40% of the weight of the nanoparticle may comprise the active agent.

The methods as described herein incorporate a pharmacologically active agent, such that the active agent may be delivered by the nanoparticle to targeted areas of the human body. In general, the active agent may include any agent capable of eliciting a pharmacological response when administered in vivo to a patient. The active agents that may be incorporated into the current invention include both hydrophobic and hydrophilic compounds. One skilled in the art will understand that hydrophobic agents tend to have poor water solubilities, while hydrophilic compounds tend to have high water solubilities. Examples of hydrophobic compounds include, but are not limited to, antineoplastic agents, cardiovascular agents, anti-inflammatory agents, antidiabetic agents, central nervous system agonists, central nervous system antagonists, immunosuppressants, and antivirals. Specific pharmacologically active agents that may be incorporated into the methods of the current invention include, but are not limited to, paclitaxel, docetaxel, irinotecan, carmustine, doxorubicin, phenesterine, piposulfan, tamoxifen, lomustine, gambogic acid, oridonin, podophyllotoxin, atorvastatin, simvastatin, fenofibrate, nifedipine, ibuprofen, indomethacin, piroxicam, glyburide, diazepam, risperidone, ziprasidone, tacrolimus, rapamycin, indinavir, ritonavir, telaprevir, lopinavir, and combinations thereof. In a preferred embodiment, the active agent comprises antineoplastic compounds, such as paclitaxel, docetaxel, irinotecan, carmustine, doxorubicin, phenesterine, piposulfan, tamoxifen, lomustine, gambogic acid, oridonin, podophyllotoxin, derivatives and analogues of the compounds listed herein, and combinations thereof. In an even more preferred embodiment, the hydrophobic active agent comprises paclitaxel and docetaxel. It is also recognized that the pharmacologically active agents may include crystalline or amorphous forms of the compounds listed herein, including the solvate and non-solvate forms.

As stated previously, the active agent may also comprise a hydrophilic compound. Examples of hydrophilic compounds within the scope of the current invention include, but are not limited to, cyclophosphamide, bleomycin, daunorubicin, epirubicin, methotrexate, fluorouracil and its analogues, platinum and analogues, vinblastine and analogues, homoharringtonine and its derivatives, actinomycin-D, mitomycin-c, and etoposide.

One skilled in the art will understand that the amount of active agent incorporated into the methods of the current invention will vary depending upon the amount of protein incorporated and will also vary depending upon the amount of nanoparticles desired to be produced. The skilled artisan will also appreciate that the active agent may be incorporated as a pure substance with 100% active agent or as a compound with less than 100% purity, without departing from the scope of the invention.

The method of the current invention also incorporates a protein that is used to encase the active agent, subsequently producing the nanoparticle of interest. Generally the protein used for the methods of the current invention includes any protein or peptide capable of denaturation and binding. Suitable examples of proteins include, but are not limited to, albumin, transferrin, including lactoferrin and ovotransferrin, insulin, endostatin, hemoglobin, myoglobin, lysozyme, immunoglobulins, α-2-macroglobulin, fibronectin, lamin, collagen, gelatin, artificial peptides and proteins, and combinations thereof. In a preferred embodiment, the proteins incorporated into the methods of the current invention comprise albumin, transferrin, insulin, endostatin, hemoglobin and combinations thereof. One skilled in the art will appreciate that the amount of protein incorporated into the method of the current invention may vary depending on the active ingredient selected, as well as the desired amount of nanoparticles. See Analytical Biochemistry Vol. 72:248-254 (1976), for general guidance on protein selection.

As stated previously, step (a) of the method of the current invention comprises preparing or obtaining the protein solution as previously described. The term "protein solution" as described in step (a) is generally defined as a solution comprising the combination of a protein and a first solvent capable of dissolving the protein of choice, and in which the protein of choice has unfolded, and in which the subsequent refolding or assembling of the protein take place. As used herein, the term "refolding" refers to a process in which an unfolded or denatured protein or peptide refolds into its suitable 3-dimensional structure. The term "assembling" refers to a process in which refolded protein or peptide is assembled to form nanoparticles. One skilled in the art will appreciate that the refolding process for proteins can be performed under a multitude of conditions. Non-limiting examples of the solvent used in the protein solution include water, saline, sugar, lyophilization protectants, and protein stabilizers. In a preferred embodiment, the first solvent may include water, saline, lyophilization protectants such as phosphate, phosphate buffered saline, acetate, glycine, tris(hydroxymethyl)aminomethane, aqueous solutions containing hydrogen peroxide, aqueous solutions comprising glutathione, sodium chloride solutions, and glucose solutions, protein stabilizers such as mycose, mannitol, sucrose, acetyltryptophan, and sodium caprylate, and combinations thereof. In a more preferred embodiment, the solvent of the protein solution comprises phosphate, acetate, and saline. Furthermore, the solvent used in the protein solution may be incorporated into the current method in any amount that is suitable for dissolving the protein and refolding or assembling the protein after unfolding. In general, the concentration of the protein solution ranges from about 0.01 M to about 1.6 M. In a preferred embodiment, the concentration ranges from about 0.03 M to about 1.5 M. In a more preferred embodiment, the concentration of the protein solution ranges from about 0.05 M to about 0.8 M. In a most preferred embodiment, the concentration ranges from about 0.1 M to about 0.3 M. The skilled artisan will understand that the amount of first solvent required to dissolve the protein will vary depending on a variety of factors including the amount of protein incorporated and the concentration of the first solvent.

It has been discovered that the reaction parameters of step (a) are important in producing the nanoparticles of the current invention, having the beneficial characteristics previously described. In general, to achieve optimal results, step (a) of the current invention is reacted at a temperature ranging from about −20° C. to about 100° C. In a preferred embodiment, step (a) of the current invention is reacted at a temperature ranging from about 50° C. to about 85° C. In a more preferred embodiment, step (a) of the current invention is reacted at a temperature ranging from about 55° C. to about 75° C. It has also been determined that the reaction of step (a) achieves optimal results when reacted at a pH from about 3 to about 9. In a preferred embodiment, the reaction of step (a) is reacted at a pH from about 5 to about 8.5. In a further preferred embodiment, step (a) is reacted at a pH from about 6 to about 8. In addition, the skilled artisan will understand that the reaction of step (a) should proceed for a period of time to allow for adequate dissolution of the protein product. Generally the period of time will vary depending on the type of protein used, the amount of protein used, the type of first solvent incorporated, the amount of first solvent, the concentration of first solvent, as well as other factors known to one of skill in the art. Generally, the skilled artisan will appreciate that the reaction as a whole, as well as the individual steps of the reaction may be performed for a time sufficient to allow the reaction to proceed. In one embodiment, the reaction is allowed to proceed for about thirty minutes to about eight hours.

The second step of the methods of the current invention comprises contacting the pharmacologically active agent with the protein solution of step (a). Additionally, step (b) is carried out in the presence of an unfolding solution. As used herein, the term "unfolding solution" refers to a solution capable of inducing a process in which proteins or peptides lose their tertiary and secondary structure. Generally, the unfolding solution should induce mild denaturation of the protein. Generally, one skilled in the art will recognize that mild denaturation refers to the situation where after unfolding/denaturation, the protein or peptide could be refolded and its suitable conformation can be restored or rearranged under certain conditions (e.g. using the refolding or assembling solution/condition). The unfolding solution may provide a reducing environment that breaks disulfide bridges, and forms hydrogen bonding bridges that allow water to disrupt the hydrophobic interactions in the interior of the protein. One skilled in the art will appreciate that a number of suitable solutions may be incorporated as the unfolding solution. Chemical agents and ingredients that may generally be used as unfolding solutions include water, strong acids, strong bases, inorganic salts, organic solvents, denaturants, and surfactants. Suitable examples of unfolding solutions include, but are not limited to, water, saline, phosphate, acetate, glycine, tris(hydroxymethyl)aminomethane, aqueous solutions containing hydrogen peroxide, aqueous solutions comprising glutathione, sodium chloride solutions, glucose solutions, methanol, ethanol, propanol, isopropanol, formaldehyde, chloroform, acetone, hydrogen sulfide 2-mercaptoethanol, dithiothreitol, guanidine, urea, perchlorate, tri-n-butylphosphine, captopril, performic acid, penicillamine, glutathione, methimazole, acetylcysteine, 3,3",3"-phosphinidynettripropionic acid, and combinations thereof. In a preferred embodiment, the unfolding solution comprises ethanol, acetone, hydrogen sulfide 2-mercaptoethanol, and urea. It has also been determined that the methods of the current invention are optimal when the unfolding solution comprises a pH ranging from about 3 to about 9. In a preferred embodiment, the unfolding solution comprises a pH ranging from about 5.5 to about 8.5.

Further, in addition to the unfolding solution, the methods of the current invention may also incorporate additional external stress to aid in the process of protein unfolding. One skilled in the art will appreciate that the external stress may include any forces capable of inducing protein unfolding. Non-limiting examples of external stress that may be incorporated to aid in protein unfolding include changes in temperature, changes in pressure, mechanical stress applied to the solution, and radiation. In one embodiment, the external stress comprises applying pressure to the reaction in the range of about 100 to about 100,000 pounds per square inch (psi) to aid in the unfolding of the protein. In another embodiment applying pressure to the reaction in the range of about 2000 to about 60,000 pounds per square inch (psi) may be used.

The methods of the current invention may further include an additional step (c) to remove impurities or salts from the nanoparticle solution formed by steps (a) and (b). In general, this step includes any process that may be used to separate the nanoparticles from the small molecules. One skilled in the art will appreciate that the method of separation may include any method known in the art to purify proteins and peptides. These processes may be performed by appropriately selecting and combining salt precipitation techniques, dialysis, gel electrophoresis, and combinations thereof. In a preferred embodiment, the methods comprise dialysis.

The methods of the current invention may also incorporate a further step (d) whereby the nanoparticle is subjected to processes to preserve the viability of the nanoparticle as a drug delivery device. In general, the preservation process includes the use of processes to dehydrate the nanoparticle to facilitate storage and transport of the nanoparticle, such that the nanoparticle may be incorporated into pharmaceutical dosage forms. Suitable examples of preservation processes that may be incorporated into the methods of the current invention include concentration, decompression drying, lyophillization, and spray drying.

In an alternative embodiment, the current invention also comprises methods for the treatment of disease in a patient. The method generally comprises the steps of producing the nanoparticles described herein according to the methods of production described herein, and administering the nanoparticle to a patient in need thereof. One skilled in the art will appreciate that the diseases that may be treated by administration of the nanoparticles described herein will vary depending on the pharmacologically active agent encased within the nanoparticle. Non-limiting examples of diseases that may be treated according to the methods of the current invention include cancer, cardiovascular diseases such as hypertension and hyperlipidemia, inflammatory processes, diabetes and other disease states that dysregulate blood-glucose levels, diseases affecting the central nervous system, neurological diseases such as Parkinson's Disease, Alzheimer's disease, and dementia, autoimmune disease states, and disease states originating from viral infection.

One skilled in the art will recognize that several variations are possible within the scope and spirit of this invention. The unfolding agents may be varied, a large variety of pharmacologically active agents may be utilized, and a wide range of proteins as well as synthesized peptides may be used in the formation of carrier. The invention will now be described in greater detail by reference to the following non-limiting examples.

The dosage forms of the present invention may also include pharmaceutically acceptable excipients. Generally, excipients are added to the formulation to ease the manufacturing process as well as to improve the performance/characteristics of the dosage form. Common excipients include diluents or bulking agents, lubricants, binders, and all other pharmaceutically acceptable excipients, all of which may be incorporated into the dosage forms of the present invention.

Diluents, or fillers, can be added in order to increase the mass of an individual dose to a size suitable for the preferred route of administration. Suitable diluents include powdered sugar, calcium phosphate, calcium sulfate, microcrystalline cellulose, glycine, trehalose, lactose, mannitol, kaolin, sodium chloride, dry starch, and sorbitol.

Binders can also be incorporated into the dosage form. Examples of suitable binders include, but are not limited to, povidone, polyvinylpyrrolidone, xanthan gum, cellulose gums such as carboxymethylcellulose, methylcellulose, hydroxyethyl cellulose, hydroxypropyl cellulose, hydroxypropyl methylcellulose, hydroxycellulose, gelatin, starch, and pregelatinized starch.

Other excipients that can be incorporated into the dosage form include, but are not limited to, preservatives, antioxidants, or any other excipient commonly used in the pharmaceutical industry. The skilled artisan will appreciate that the amount of excipients incorporated into the dosage form in conjunction with the nanoparticles will vary depending on the desired characteristics of the dosage form.

EXAMPLES

The examples, which are intended to be purely exemplary of the invention, should therefore not be considered to limit the invention in any way. Efforts have been make to ensure accuracy with respect to numbers used, but some experimental errors and deviations should be accounted for.

Example 1

Preparation of Paclitaxel-Albumin Nanoparticles 100 mg of albumin was dissolved in 10 ml 0.1M phosphate buffer pH 6.0 containing 0.5 mg/mL ethylenediaminetetraacetate and 0.05M mercaptoethanol. The reaction was carried out for two hours. At the end of reaction, the protein was precipitated and washed with 5% trichloroacetic acid. Next, 16 mg paclitaxel was dissolved in 1.6 mL ethanol and mixed with the precipitated protein. After 10 minutes mixing, 50 mL 0.1M phosphate buffer pH 8.0 was added to dissolve the mixture. The resulting dispersion is translucent, and the typical diameter of the resulting paclitaxel particles was 80 nm-200 nm (BIC 90 plus particle size analyzer). HPLC analysis of the paclitaxel content revealed that more than 90% of the paclitaxel was encapsulated into the albumin.

Example 2

Preparation of Paclitaxel-Albumin Nanoparticles without Protein Precipitation 100 mg of albumin was dissolved in 50 mL tris-buffer (pH 7.4) with stifling at 37° C. and 350 µL mercaptoethanol was added. The unfolding reaction was carried out for 10 minutes. Two mL of ethanol solution containing 20 mg paclitaxel was added. After 30 minutes, the sample was dialyzed in tris-buffer (pH 7.4) for 24 h. The dispersion was further lyophilized for 48 hours. The resulting cake could be easily reconstituted to the original dispersion by addition of sterile water or saline. The particle size after reconstitution was the same as before lyophillization. The typical diameter of the resulting paclitaxel particles was 80 nm-200 nm (BIC 90 plus particle size analyzer). HPLC analysis of the paclitaxel content revealed that more than 90% of the paclitaxel was encapsulated into the nanoparticles.

Example 3

Preparation of Paclitaxel-Albumin Nanoparticles 100 mg human albumin was dissolved in 10 ml buffer, pH 4.8, and kept in an ice bath for 30 minutes. 7.5 mL cold acetone (0° C.) was added (to induce precipitation) and kept in the ice bath for an additional 60 minutes. The solution was then centrifuged and precipitates were collected. A 10 mg/ml acetone solution of paclitaxel was added and mixed with the precipitates by applying sonication. A physiological buffer was added and mixed using a magnetic stirrer to form a solution. The mean particle size of the paclitaxel-albumin nanoparticles thus obtained was analyzed using BIC 90 plus particle size analyzer, and found to be 150-220 nm. The nanoparticle solution was then dried by lyophillization. The freeze-dried cake was reconstituted. The paclitaxel loading of the nanoparticles was 8.3% using a HPLC assay.

Additional experiments showed that glycine, mannitol, trehalose or lactose can be used as a bulking agent for lyophillization while use of lactose resulted in smaller nanoparticles. Further, additional experiments showed that the precipitation or unfolding process above could also be conducted by salt solution at a temperature ranging from about 55° C. to about 75° C.

Example 4

Preparation of Paclitaxel-Transferrin Nanoparticles without Protein Precipitation 100 mg of transferrin dissolved in 50 ml tris-buffer (pH 7.4) with stirring at 25° C. and 350 uL mercaptoethanol was added. The unfolding reaction was carried out for 10 minutes. 1 mL of ethanol solution containing 10 mg paclitaxel was then added. The mean particle size was 154.4 nm (BIC 90 plus particle size analyzer). The theoretical paclitaxel loading of the nanoparticles was 9.0%.

Example 5

Preparation of Docetaxel-Transferrin Nanoparticles without Protein Precipitation 100 mg of transferrin was dissolved in 50 mL tris-buffer (pH 7.4) with stirring at 25° C. and 350 uL mercaptoethanol was added. The unfolding reaction was carried out for 10 minutes. 5 ml of ethanol solution containing 50 mg docetaxel was added. The solution turned to light blue without any precipitation. The mean particle size after reconstitution was 177.1 nm (BIC 90 plus particle size analyzer). The theoretical docetaxel loading of the nanoparticles was 33.3%.

Example 6

Preparation of Gambogic Acid-Albumin Nanoparticles 100 mg albumin was first dissolved in 10 ml water. The resulting solution was mixed with an equal volume of trichloroacetic acid and centrifuged to remove the supernatant. An ethanol solution of gambogic acid was then added to the obtained protein precipitate followed by addition of 50 ml TRIS buffer (pH 8.0), stirred until complete dissolution of the protein precipitate. The mean particle size of the gambogic acid-albumin nanoparticles thus obtained was analyzed using BIC 90 plus particle size analyzer, and found to be 110 nm. The theoretical gambogic acid loading of the nanoparticles was 9.0%.

Example 7

Preparation of Paclitaxel-Hemoglobin Nanoparticles 10 mL of 3% hemoglobin aqueous solution was slowly added to 300 mL acetone solution containing 3 mL 2N HCl at −20° C. The solution was then agitated vigorously for 15 minutes followed by centrifugation for 15 minutes. After the residual acetone evaporated, the precipitate collected was dissolved in cold deionized water. The solution underwent dialysis first in deionized water for 5 hours at 2° C., then in 0.0016M $NaHCO_3$ solution for 30 hours. Globin solution was obtained by filtration.

To 7 mL of the above globin solution, 28 ml of deionized water was added to obtain a solution of about 1 mg/mL. Next, 0.7 mL of paclitaxel solution in ethanol (10 mg/mL) was then added at low temperature (2-8° C.) and stirred until a light blue solution is obtained. There was no precipitation in the solution. The mean particle size of the paclitaxel-globin nanoparticles thus obtained was analyzed using BIC 90 plus particle size analyzer, and found to be 301.8 nm. The theoretical paclitaxel loading of the nanoparticles was 9.0%

Example 8

Preparation of Paclitaxel-Albumin Nanoparticles in Acetyltryptophan Buffer

One hundred milligrams of albumin was dissolved in the 50 mL solution containing 0.16 mM acetyltryptophan and 0.16 mM sodium caprylate. The solution was stirred at 37° C. and 350 mL mercaptoethanol was added. The unfolding reaction was carried out for 10 minutes. Next, 1.5 mL of ethanol solution containing 15 mg paclitaxel was added and stirred until the light blue solution was obtained. The typical diameter of the resulting paclitaxel-albumin particles is 130 nm determined by BIC 90 plus particle size analyzer.

Example 9

Preparation of Paclitaxel-Albumin Nanoparticles in Glucose Solution

One hundred milligrams of albumin was dissolved in the 50 mL of 5% w/v glucose solution with stifling at 37° C. and 350 mL mercaptoethanol was added. The unfolding reaction was carried out for 10 minutes. Additionally, 1.5 mL of ethanol solution containing 15 mg paclitaxel was added and stirred until a light blue solution was obtained. The typical diameter of the resulting paclitaxel-albumin particles was 130 nm determined by BIC 90 plus particle size analyzer.

Example 10

Effects of pH on Nanoparticle Sizes

Figure 1:
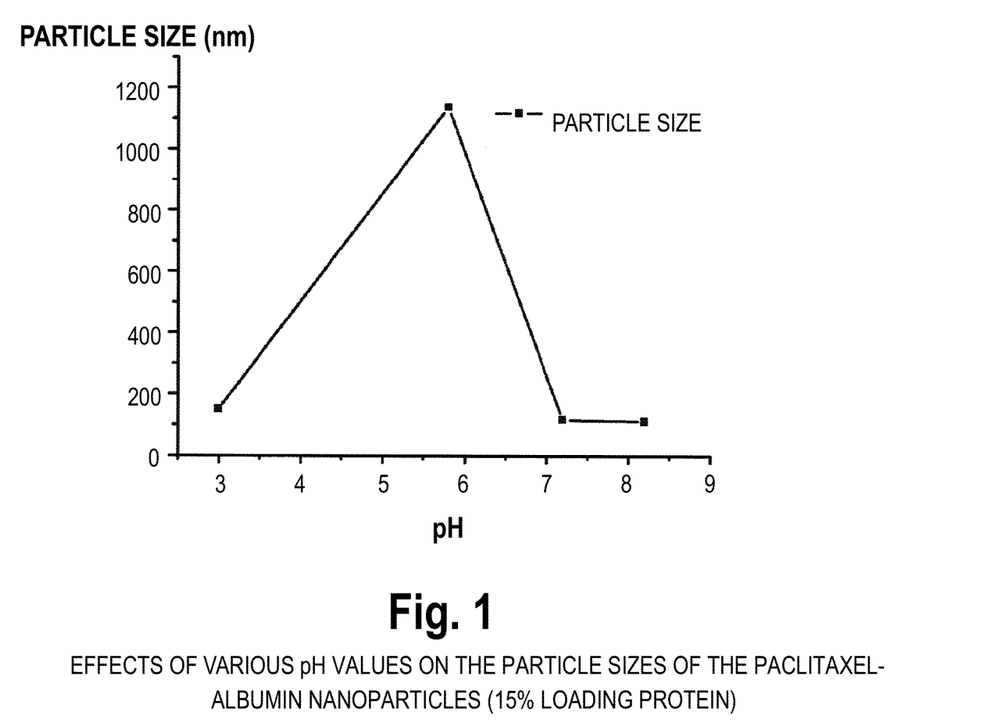
FIG. 1 shows the effects of various pH values on the particle size of the paclitaxel-albumin nanoparticles.

In accord with the teachings of the current invention, phosphate buffer with various pH levels was utilized to prepare nanoparticles and evaluated for its effect on the sizes of different nanoparticles. All of the protein solutions were fed with 15% paclitaxel (10 mg/mL). Diameters of the nanoparticles were analyzed in isothermal conditions. The results are shown in FIG. 1.

Example 11

Characterization of Paclitaxel-Albumin Nanoparticles Using Dynamic Light Scattering (DLS)

Figure 2:
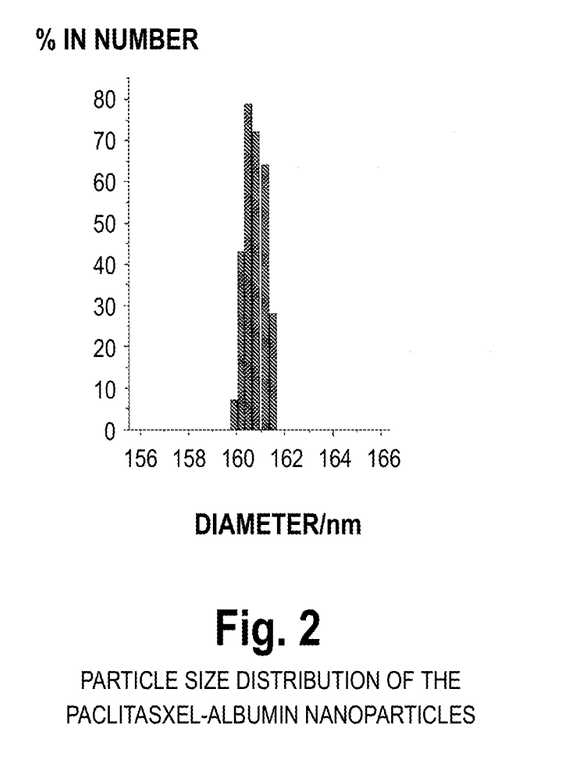
FIG. 2 shows a graph with the particle size distribution of paclitaxel-albumin nanoparticles.

The particle size distribution of paclitaxel-albumin nanoparticles produced according to the methods of the current invention was examined using the BIC 90 plus Particle Size Analyzer. It is shown in FIG. 2 that the average particle size is 121 nm with a narrow size distribution.

Example 12

Transmission Electron Microscopy of Nanoparticles

Figure 3:
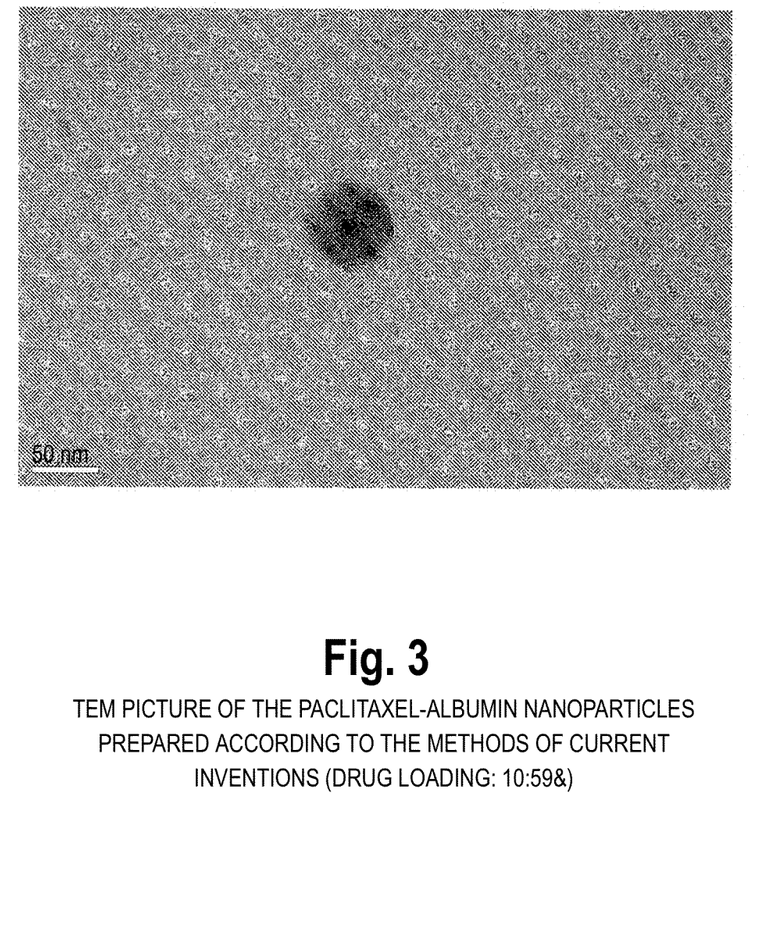
FIG. 3 shows a TEM picture of the paclitaxel-albumin nanoparticles prepared according to the methods of the current inventions (drug loading: 10.59%).

Nanoparticles loaded with 10.59% paclitaxel were prepared according to the methods of the current invention. The TEM images were examined using the EM-2100 200 kV high resolution transmission electron microscope (Japan). FIG. 3 shows the results and the nanoparticles were revealed to be spherical in shape.

Example 13

Stability Study of the Reconstituted Paclitaxel-Albumin Nanoparticles

The lyophilized paclitaxel-albumin cake was reconstituted in normal saline (NS) at 5 mg/ml, in 5% glucose solution (GS) at 5 mg/ml, and in calf serum (CS) at 2 mg/ml respectively. After storing at different temperatures (25° C. and 37° C.) for 36 hours, the mean particle size of the paclitaxel-albumin nanoparticles (DLS, BIC 90 plus Particle Size Analyzer) remained unchanged. No precipitate was observed. Results are summarized in Table 1.

TABLE 1

| Diameter (nm) | 0 h | 3 h | 6 h | 12 h | 18 h | 24 h | 36 h |
| --- | --- | --- | --- | --- | --- | --- | --- |
| NS, 25° C. | 113.8 | 111.5 | 108.1 | 108.0 | 108.9 | 106.2 | 108.8 |
| GS, 25° C. | 113.7 | 123.3 | 122.1 | 121.1 | 123.1 | 116.5 | 125.3 |
| CS, 37° C. | 119.7 | 151.8 | 144.6 | 147.1 | 160.4 | 156.8 | 184.9 |

Example 14

Investigation of Paclitaxel-Transferrin Nanoparticles

Additional experiments preparing paclitaxel-transferrin nanoparticles were carried out. It was found that (1) in addition to tris-buffer, saline solution can also be used to dissolve transferrin; (2) paclitaxel-transferrin nanoparticles can be obtained at pH 3-8.5 with an optimal range of pH 6-7.5 for obtaining nanoparticles of higher drug loading and more desirable stability; and (3) cane sugar, glucose, glycine, and mycose can be used as an effective bulking agent for lyophillization or decompression drying.

Example 15

Stability Study of the Reconstituted Paclitaxel-Transferrin Nanoparticles

The lyophilized paclitaxel-transferrin cake was reconstituted in normal saline (NS) at 5 mg/ml, in 5% glucose solution (GS) at 5 mg/ml, and in calf serum (CS) at 2 mg/ml respectively. After storing at different temperatures (25° C. and 37° C.) for 36 hours, the mean particle size of the paclitaxel-transferrin nanoparticles (DLS, BIC 90 plus Particle Size Analyzer) remained unchanged. No precipitate was observed. Results are summarized in Table 2.

TABLE 2

| Diameter (nm) | 0 h | 3 h | 6 h | 12 h | 18 h | 24 h | 36 h |
|---|---|---|---|---|---|---|---|
| NS, 25° C. | 143.2 | 132.7 | 132.9 | 133.4 | 134.0 | 127.3 | 139.6 |
| GS, 25° C. | 168.4 | 152.3 | 146.5 | 144.0 | 147.5 | 144.7 | 145.6 |
| CS, 37° C. | 118.8 | 139.3 | 152.7 | 165.6 | 171.5 | 177.6 | 228.8 |

Example 16

Characterization of Paclitaxel-Albumin Nanoparticles Using Transmission Electron Microscopy (TEM)

Two or three drops of each paclitaxel-albumin nanoparticles solution were deposited on a carbon-coated copper grids (200 mesh) respectively. After 2 minutes, the grid was lifted off, excess solution was removed by filter paper and then air dried. The nanoparticle images were examined using the EM-2100 200 kV high resolution transmission electron microscope (Japan).

Figure 4:
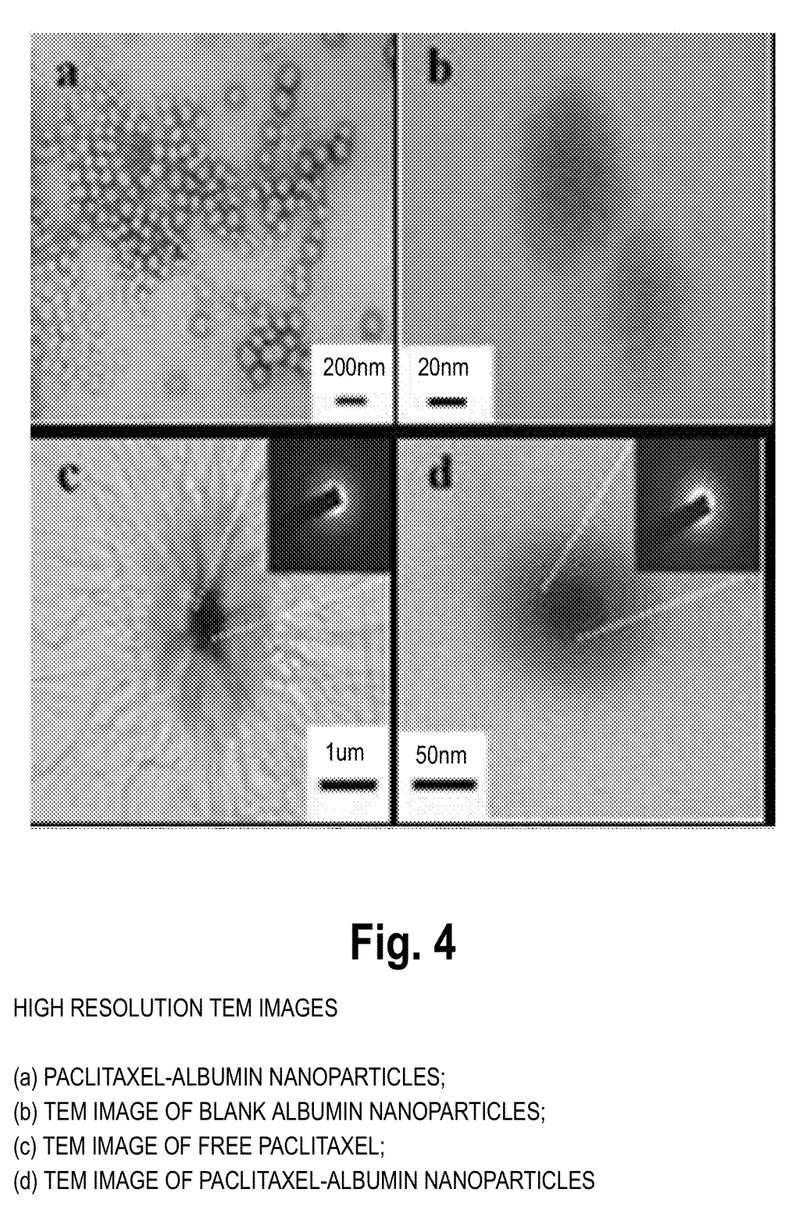
FIG. 4 shows the transmission electron microscopy picture of an albumin nanoparticle loaded with 10-20% paclitaxel by weight of the nanoparticle.

Results of TEM: The TEM images of the samples are shown in FIG. 4. It was found that (a) paclitaxel-albumin nanoparticles are spherical in shape (b) blank albumin nanoparticles are of irregular shape with an average primary particle size of about 100 nm; (c) free paclitaxel shows a high electron-dense image at the center surrounded by stick-shaped structure. (d) paclitaxel-albumin nanoparticles show a core/shell structure.

Example 17

Characterization of Solid State of Paclitaxel in Nanoparticles by X-Ray Powder Diffraction (XRD)

Paclitaxel is crystalline with extremely low aqueous solubility (1 μg/ml for the dehydrate form). Thus, amorphous paclitaxel is highly beneficial for injection due to its higher apparent solubility. To evaluate the solid state characteristics of paclitaxel in the paclitaxel nanoparticles of the present invention, x-ray powder diffraction technique was used. Four samples were prepared for x-ray powder diffraction analysis: (a) paclitaxel; (b) albumin nanoparticles; (c) paclitaxel-albumin nanoparticles (drug loading=12.9%); (d) physical mixture of albumin and paclitaxel (12.9%). Data of each sample was collected over two-theta (CuKa) angle range from 5 to 50 degrees using a powder diffractometer (ARL, X'TRA, Applied Research Laboratories, Switzerland).

Figure 5:
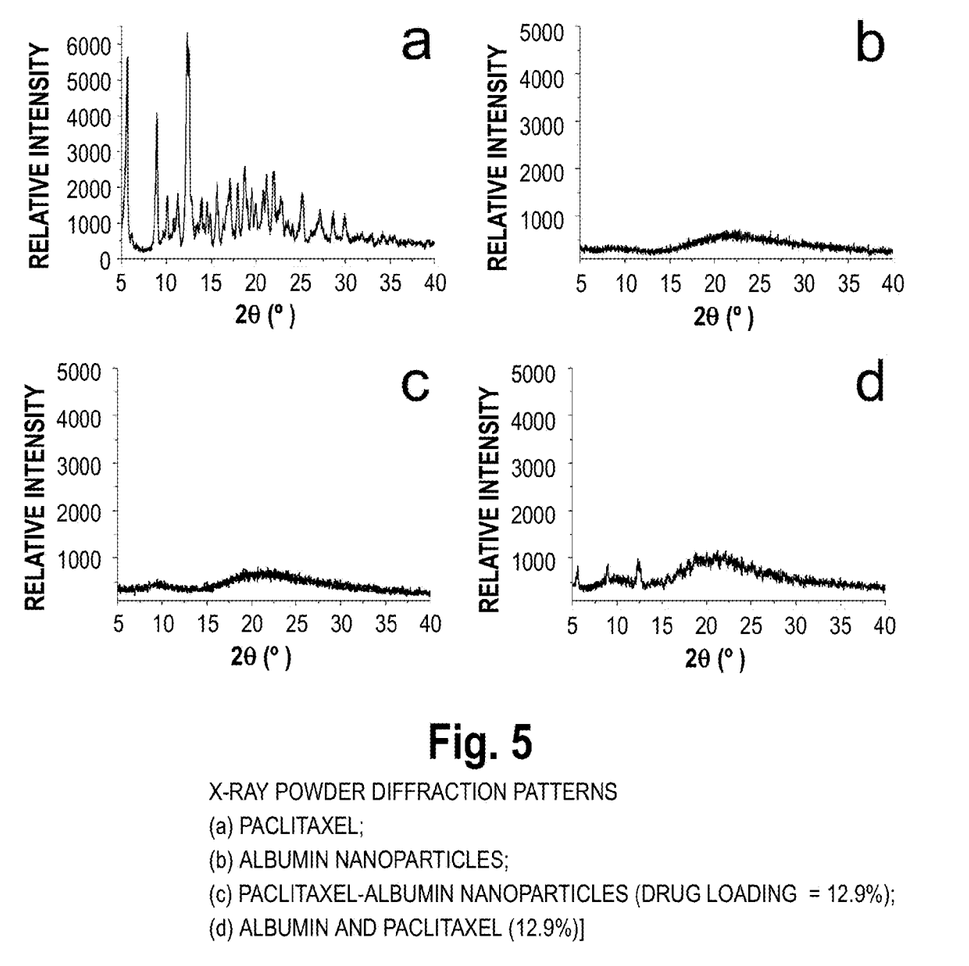
FIG. 5 shows the X-ray powder diffraction patterns of paclitaxel drug substance, albumin, physical mixture of albumin and paclitaxel and paclitaxel-albumin nanoparticles.

Results provided in FIG. 5 show that (a) XRD pattern of paclitaxel exhibits peaks characteristic of crystalline drug; (b) XRD pattern of albumin nanoparticles exhibits a broad halo peak in the 2θ range of 15-45°, which is characteristic of an amorphous phase of albumin (c) XRD pattern of paclitaxel-albumin nanoparticles also exhibits a broad halo peak in the 2θ range of 15-45°, which indicates the presence of amorphous paclitaxel in nanoparticles. (d) XRD pattern of the physical mixture of paclitaxel-albumin containing the same level of paclitaxel as that of the paclitaxel-albumin nanoparticles (12.9%) indicates the presence of crystalline paclitaxel and amorphous albumin in the sample. Therefore, it is concluded that the paclitaxel-albumin nanoparticles produced by the present invention is amorphous in nature.

Example 18

Dispersion Study of Paclitaxel-Albumin Nanoparticles

Figure 6:
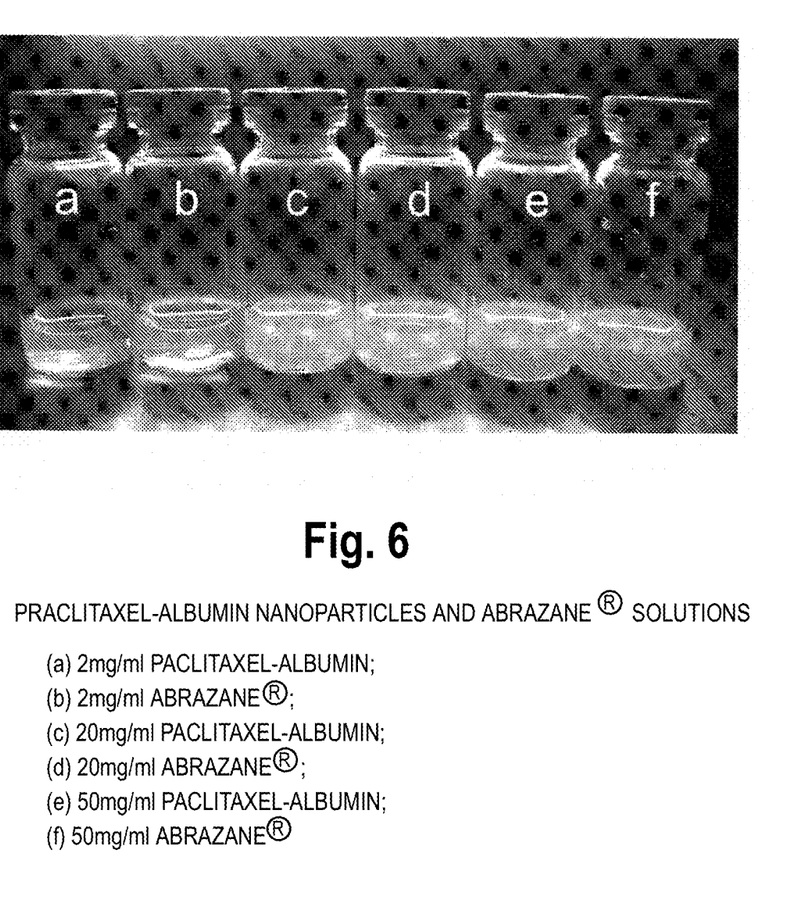
FIG. 6 shows the redispersion of paclitaxel-albumin nanoparticles and the control reference, Abraxane® in various solutions.

The lyophilized paclitaxel-albumin cake according to the methods of the current invention and the listed drug Abraxane® was reconstituted in water at following protein concentration: (a, b) 2 mg/mL; (c,d) 20 mg/mL; (e,f) 50 mg/mL, respectively. The images of these samples are illustrated in FIG. 6. As shown in FIG. 6, stable translucent colloidal dispersions of paclitaxel-albumin nanoparticles were obtained with all three samples.

What is claimed is:

1. A method for the preparation of nanoparticles fully encasing a pharmacologically active agent within a protein which has been unfolded and subsequently refolded or assembled for in vivo delivery, wherein said method comprises the following steps:
   (a) preparing or obtaining a protein solution comprising said protein in a first solvent; and
   (b) contacting said pharmacologically active agent with said protein solution of step (a) in the presence of an unfolding solution, thereby causing unfolding of said protein, and subsequent refolding or assembling of said protein to fully encase said pharmacologically active agent within said protein,
   wherein the pharmacologically active agent is selected from the group consisting of: paclitaxel, docetaxel, gambogic acid, doxorubicin, rapamycin, tacrolimus, and combinations thereof.

2. The method of claim 1, wherein said nanoparticles comprise about 1% to about 40% of pharmacologically active agent by total weight of the nanoparticle.

3. The method of claim 1, wherein said protein is selected from the group consisting of: albumin, transferrin, insulin, endostatin, hemoglobin, myoglobin, lysozyme, immunoglobulins, α-2-macroglobulin, fibronectin, lamin, collagen, gelatin, artificial peptides and proteins, and combinations thereof.

4. The method of claim 1, wherein said in vivo delivery comprises delivery of said nanoparticles by a route of administration is selected from the group consisting of: oral, intravenous, subcutaneous, intraperitoneal, intrathecal, intranasal, intramuscular, inhalational, topical, transdermal, rectal, vaginal, and combinations thereof.

5. The method of claim 1, wherein said first solvent of step (a) is selected from the group consisting of: water, saline, sugar, a lyophilization protectant, and a protein stabilizer.

6. The method of claim 5, wherein said lyophilization protectant is selected from the group consisting of: phosphate, phosphate buffered saline, acetate, glycine, tris(hydroxymethyl)aminomethane, aqueous solutions containing hydrogen peroxide, aqueous solutions comprising glutathione, sodium chloride solutions, glucose solutions, and combinations thereof.

7. The method of claim 5, wherein said protein stabilizer is selected from the group consisting of: mycose, mannitol, sucrose, acetyltryptophan, sodium caprylate, and combinations thereof.

8. The method of claim 1, wherein said unfolding solution of step (b) is selected from the group consisting of: water, strong acids, strong bases, inorganic salts, organic solvents, denaturants, and surfactants.

9. The method of claim 8, wherein said organic solvents are selected from the group consisting of: methanol, ethanol, propanol, isopropanol, formaldehyde, chloroform, acetone, hydrogen sulfide and combinations thereof.

10. The method of claim 8, wherein said denaturants are selected from the group consisting of: 2-mercaptoethanol, dithiothreitol, guanidine, urea, perchlorate, tri-n-butylphosphine, captopril, performic acid, penicillamine, glutathione, methimazole, acetylcysteine, 3,3",3"-phosphinidynettripropionic acid and combinations thereof.

11. The method of claim 8, wherein said inorganic salts are selected from the group consisting of: water, saline, phosphate, acetate, glycine, tris(hydroxymethyl)aminomethane, aqueous solutions containing hydrogen peroxide, aqueous solutions comprising glutathione, sodium chloride solutions, glucose solutions and combinations thereof.

12. The method of claim 1, further comprising:
(c) subjecting said nanoparticles to a dialysis or filtration step to remove excess chemicals or to obtain a more concentrated solution.

13. The method of claim 12, further comprising:
(d) subjecting said concentrated solution of nanoparticles of step (c) to a dehydration process to produce preserved nanoparticles capable of incorporation into a pharmaceutical dosage form.

14. The method of claim 13, wherein said dehydration process is selected from the group consisting of: lyophilization, decompression drying, and spray drying.

15. A method for the preparation of nanoparticles fully encasing a hydrophobic pharmacologically active agent within a protein which has been unfolded and subsequently refolded or assembled for in vivo delivery, wherein said method comprises the following steps:
(a) preparing or obtaining a protein solution comprising said protein in a first solvent at a temperature ranging from about −20° C. to about 100° C., and a pH ranging from about 3 to about 9; and
(b) contacting said hydrophobic pharmacologically active agent with said solution of step (a) in the presence of an unfolding solution, thereby causing unfolding of said protein, and subsequent refolding or assembling of said protein to fully encase said pharmacologically active agent within said protein;
wherein said nanoparticles have a diameter ranging from about 5 nm to about 2000 nm and said nanoparticles comprise about 1% to about 40% of pharmacologically active agent by total weight of the nanoparticle;
wherein said hydrophobic pharmacologically active agent is selected from the group consisting of: paclitaxel, docetaxel, doxorubicin, gambogic acid, tacrolimus, rapamycin, and combinations thereof;
wherein said protein is selected from the group consisting of: albumin, transferrin, insulin, endostatin, hemoglobin, myoglobin, lysozyme, immunoglobulins, α-2-macroglobulin, fibronectin, lamin, collagen, gelatin, artificial peptides and proteins, and combinations thereof;
wherein said first solvent is selected from the group consisting of: water, saline, phosphate, acetate, glycine, tris(hydroxymethyl)aminomethane, aqueous solutions containing hydrogen peroxide, aqueous solutions comprising glutathione, sodium chloride solutions, glucose solutions, mycose, mannitol, sucrose, acetyltryptophan, sodium caprylate and combinations thereof; and
wherein said unfolding solution is selected from the group consisting of: water, saline, phosphate, acetate, glycine, tris(hydroxymethyl)aminomethane, aqueous solutions containing hydrogen peroxide, aqueous solutions comprising glutathione, sodium chloride solutions, glucose solutions, methanol, ethanol, propanol, isopropanol, formaldehyde, chloroform, acetone, hydrogen sulfide, 2-mercaptoethanol, dithiothreitol, guanidine, urea, perchlorate, tri-n-butylphosphine, captopril, performic acid, penicillamine, glutathione, methimazole, acetylcysteine, 3,3",3"-phosphinidynettripropionic acid, and combinations thereof.

16. The method of claim 15, wherein said unfolding solution is selected from the group consisting of: water, saline, phosphate, acetate, glycine, tris(hydroxymethyl)aminomethane, sodium chloride solutions, ethanol, acetone, hydrogen sulfide, 2-mercaptoethanol, urea, and combinations thereof.

17. The method of claim 15, further comprising:
(c) dialyzing or filtering said nanoparticles to remove excess chemicals to obtain a more concentrated solution.

18. The method of claim 17, further comprising:
(d) subjecting said concentrated solution of nanoparticles of step (c) to a dehydration process to produce preserved nanoparticles capable of incorporation into a pharmaceutical dosage form.

19. The method of claim 18, wherein said dehydration process is selected from the group consisting of: lyophilization, decompression drying, and spray drying.

20. A method for the preparation of nanoparticles fully encasing paclitaxel within a protein which has been unfolded and subsequently refolded or assembled for in vivo delivery, wherein said method comprises the following steps:
(a) preparing or obtaining a protein solution comprising said protein in a first solvent at a temperature ranging from about 55° C. to about 75° C., and a pH ranging from about 6 to about 8;
(b) contacting said paclitaxel with said protein solution of step (a) in the presence of an unfolding solution, thereby causing unfolding of said protein, and subsequent refolding or assembling of said protein to fully encase said paclitaxel within said protein;
(c) performing dialysis or filtration to remove excess chemicals or to obtain a more concentrated solution; and
(d) subjecting said concentrated solution of nanoparticles of step (c) to a dehydration process to produce preserved nanoparticles capable of incorporation into a pharmaceutical dosage form;
wherein said nanoparticles have an average diameter ranging from about 50 nm to about 300 nm and said nanoparticles comprise about 1% to about 40% of paclitaxel by total weight of the nanoparticle;
wherein said unfolding solution is selected from the group consisting of water, saline, phosphate, acetate, glycine, tris(hydroxymethyl)aminomethane, sodium chloride solution, ethanol, acetone, hydrogen sulfide, 2-mercaptoethanol, urea, and combinations thereof; and
wherein said protein is selected from the group consisting of albumin, transferrin, insulin, endostatin, and hemoglobin.

21. A method for the preparation of nanoparticles fully encasing docetaxel within a protein which has been unfolded and subsequently refolded or assembled for in vivo delivery, wherein said method comprises the following steps:
  (a) preparing or obtaining a protein solution comprising said protein in a first solvent at a temperature ranging from about 55° C. to about 75° C., and a pH ranging from about 6 to about 8;
  (b) contacting said docetaxel with said protein solution of step (a) in the presence of an unfolding solution, thereby causing unfolding of said protein, and subsequent refolding or assembling of said protein to fully encase said docetaxel within said protein;
  (c) dialyzing or filtering said nanoparticles to remove excess chemicals to obtain a more concentrated solution; and
  (d) subjecting said concentrated solution of nanoparticles of step (c) to a dehydration process to produce preserved nanoparticles capable of incorporation into a pharmaceutical dosage form;
  wherein said nanoparticles have an average diameter ranging from about 50 nm to about 300 nm and said nanoparticles comprise about 1% to about 40% of docetaxel by total weight of the nanoparticle;
  wherein said unfolding solution is selected from the group consisting of water, saline, phosphate, acetate, glycine, tris(hydroxymethyl)aminomethane, sodium chloride solution, ethanol, acetone, hydrogen sulfide, 2-mercaptoethanol, urea, and combinations thereof; and
  wherein said protein is selected from the group consisting of albumin, transferrin, insulin, endostatin, and hemoglobin.

22. A method of treating cancer comprising the steps of:
  (a) producing a nanoparticle according to the process described in claim 15; and
  (b) administering said nanoparticle to a patient in need thereof.

23. A nanoparticle comprising a pharmacologically active agent fully encased within a protein which has been unfolded and subsequently refolded or assembled, wherein said nanoparticle is suitable for in vivo delivery, and wherein said nanoparticle is produced according to the following steps:
  (a) preparing or obtaining a protein solution comprising said protein in a first solvent at a temperature ranging from about −20° C. to about 100° C., and a pH ranging from about 3 to about 9; and
  (b) contacting said hydrophobic pharmacologically active agent with said protein solution of step (a) in the presence of an unfolding solution, thereby causing unfolding of said protein, and subsequent refolding or assembling of said protein to fully encase said pharmacologically active agent within said protein;
  wherein said nanoparticles have a diameter ranging from about 5 nm to about 2000 nm and said nanoparticles comprise about 1% to about 40% of pharmacologically active agent by total weight of the nanoparticle;
  wherein said hydrophobic pharmacologically active agent is selected from the group consisting of: paclitaxel, docetaxel, doxorubicin, gambogic acid, tacrolimus, rapamycin, and combinations thereof;
  wherein said protein is selected from the group consisting of: albumin, transferrin, insulin, endostatin, hemoglobin, myoglobin, lysozyme, immunoglobulins, α-2-macroglobulin, fibronectin, lamin, collagen, gelatin, artificial peptides and proteins, and combinations thereof;
  wherein said first solvent is selected from the group consisting of: water, saline, phosphate, acetate, glycine, tris(hydroxymethyl)aminomethane, aqueous solutions containing hydrogen peroxide, aqueous solutions comprising glutathione, sodium chloride solutions, glucose solutions, and combinations thereof; and
  wherein said unfolding solution is selected from the group consisting of: water, saline, phosphate, acetate, glycine, tris(hydroxymethyl)aminomethane, aqueous solutions containing hydrogen peroxide, aqueous solutions comprising glutathione, sodium chloride solutions, glucose solutions, methanol, ethanol, propanol, isopropanol, formaldehyde, chloroform, acetone, hydrogen sulfide, 2-mercaptoethanol, dithiothreitol, guanidine, urea, perchlorate, tri-n-butylphosphine, captopril, performic acid, penicillamine, glutathione, methimazole, acetylcysteine, 3,3",3"-phosphinidynettripropionic acid, and combinations thereof.

24. A nanoparticle comprising paclitaxel fully encased within a protein which has been unfolded and subsequently refolded or assembled, wherein said nanoparticle is suitable for in vivo delivery, and wherein said nanoparticle is produced according to the following steps:
  (a) preparing or obtaining a protein solution comprising said protein in a first solvent at a temperature ranging from about 55° C. to about 75° C., and a pH ranging from about 6 to about 8;
  (b) contacting said paclitaxel with said protein solution of step (a) in the presence of an unfolding solution, thereby causing unfolding of said protein, and subsequent refolding or assembling of said protein to fully encase said paclitaxel within said protein;
  (c) dialyzing or filtering said nanoparticles to remove excess chemicals to obtain a more concentrated solution; and
  (d) subjecting said concentrated solution of nanoparticles of step (c) to a dehydration process to produce preserved nanoparticles capable of incorporation into a pharmaceutical dosage form;
  wherein said nanoparticles have an average diameter ranging from about 50 nm to about 300 nm and said nanoparticles comprise about 1% to about 40% of paclitaxel by total weight of the nanoparticle;
  wherein said unfolding solution is selected from the group consisting of water, saline, phosphate, acetate, glycine, tris(hydroxymethyl)aminomethane, sodium chloride solution, ethanol, acetone, hydrogen sulfide, 2-mercaptoethanol, urea, and combinations thereof; and
  wherein said protein is selected from the group consisting of albumin, transferrin, insulin, endostatin, and hemoglobin.

25. A nanoparticle comprising docetaxel fully encased within a protein which has been unfolded and subsequently refolded or assembled, wherein said nanoparticle is suitable for in vivo delivery, and wherein said nanoparticle is produced according to the following steps:
  (a) preparing or obtaining a protein solution comprising said protein in a first solvent at a temperature ranging from about 55° C. to about 75° C., and a pH ranging from about 6 to about 8;
  (b) contacting said docetaxel with said protein solution of step (a) in the presence of an unfolding solution, thereby causing unfolding of said protein, and subsequent refolding or assembling of said protein to fully encase said docetaxel within said protein;

(c) dialyzing or filtering said nanoparticles to remove excess chemicals to obtain a more concentrated solution; and
(d) subjecting said concentrated solution of nanoparticles of step (c) to a dehydration process to produce preserved nanoparticles capable of incorporation into a pharmaceutical dosage form;
wherein said nanoparticles have an average diameter ranging from about 50 nm to about 300 nm and said nanoparticles comprise about 1% to about 40% of docetaxel by total weight of the nanoparticle;
wherein said unfolding solution is selected from the group consisting of water, saline, phosphate, acetate, glycine, tris(hydroxymethyl)aminomethane, sodium chloride solution, ethanol, acetone, hydrogen sulfide, 2-mercaptoethanol, urea, and combinations thereof; and
wherein said protein is selected from the group consisting of albumin, transferrin, insulin, endostatin, and hemoglobin.

* * * * *